US00PP28045P3

(12) United States Plant Patent
Byrne et al.

(10) Patent No.: US PP28,045 P3
(45) Date of Patent: May 23, 2017

(54) PEACH TREE NAMED 'ROYAL ZEST ONE'

(50) Latin Name: *Prunus persica*
Varietal Denomination: Royal Zest One

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 31 days.

(21) Appl. No.: 14/544,510

(22) Filed: Jan. 13, 2015

(65) Prior Publication Data

US 2016/0205838 P1 Jul. 14, 2016

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

| | | | | | |
|---|---|---|---|---|---|
| PP6,472 | P | * | 12/1988 | Zaiger et al. | Plt./198 |
| PP7,290 | P | * | 8/1990 | Zaiger et al. | Plt./197 |
| PP14,627 | P3 | * | 3/2004 | Byrne et al. | Plt./197 |
| PP14,629 | P3 | * | 3/2004 | Byrne et al. | Plt./198 |

OTHER PUBLICATIONS

Clemson University—Variety Evaluations June Gold 2001, retrieved on Jul. 13, 2016, retrieved from the Internet at <http://www.clemsonpeach.org/index.php?p=181&e=683> one page.*
Texas A&M AgriLife 2013 Royal and Golden Zest Peaches, retrieved on Jul. 14, 2016, retrieved from the Internet at <http://aggie-horticulture.tamu.edu/fruit-nut/files/2010/10/Royal-Golden-Zest-Peaches-one-Pager-Feb-8-2013.pdf> 1 page.*
The Brooks and Olmo Register of Fruit and Nut Varieties, 3rd Ed., American Society of Horticultural Science Press, Alexandria, VA, 1997. p. 396.
Brooks, R. M. 1958. Double Delight, Earligold, and June Gold peaches. Fruit Var. J. 3:22. 4 pp.

* cited by examiner

*Primary Examiner* — June Hwu
(74) *Attorney, Agent, or Firm* — Ramey & Schwaller, LLP

(57) ABSTRACT

Disclosed is a new variety of *Prunus persica* named 'Royal Zest One'. This new variety, which requires approximately 600 chilling units of dormancy, is considered to be a peach tree of early season maturity, which produces yellow fleshed fruit that are firm, attractively colored, and suitable for the regional fresh fruit market.

5 Drawing Sheets

Latin name of the genus and species of the plant claimed: *Prunus persica.*

Variety denomination: 'Royal Zest One'.

BACKGROUND OF THE INVENTION

Field of the Invention

This invention relates to peach trees and, more specifically, to peach trees referred to as a variety of *Prunus persica* named 'Royal Zest One'. 'Royal Zest One', which requires approximately 600 chilling units of dormancy, produces an exceptionally high quality, firm clingstone peach that matures early in the season.

SUMMARY OF THE INVENTION

The 'Royal Zest One' peach is characterized as to novelty and is otherwise noteworthy by producing fruit that ripens in the early season; is considered high quality; and which is firm and has an attractive coloration. In this regard, the present variety of peach tree bears fruit that are ripe for commercial harvesting and shipment in mid to late May, when the fruit is grown in medium chill zone of Texas. 'Royal Zest One' ripens 10-14 days earlier than 'June Gold' peach, (U.S. Plant Pat. No. 1,884). Additionally, the new variety exhibits the potential to be commercialized in regions that have chilling requirements that are relatively low.

Origin of the Variety

The present peach tree was the result of an ongoing Stone Fruit Breeding Program of Texas A & M University, College Station, Brazos County, Tex. To this end, both controlled and hybrid crosses are made each year in order to produce seedling populations from which improved progenies are evaluated and selected.

'Royal Zest One' was selected as a seedling and given the selection name of TX4B235 at the Texas A & M University Horticultural Farm in College Station, Tex. in 2003 in a population of seedlings that resulted from a cross between a yellow-fleshed, medium chill peach selection (TX2293-1='Flordaking' (not patented, Andrews et al., 1979 open pollinated) as a female parent and the California cultivar 'Rich Lady', (U.S. Plant Pat. No. 7,290) an early/mid-season, yellow-fleshed peach that was released by Zaiger Genetics as the male (pollen) parent. 'Rich Lady' is an open pollinated seedling from 'Amparo' (U.S. Plant Pat. No. 6,472). Resulting seed from this cross were planted in 2000 at the Texas A & M University Horticultural Farm in College Station, Tex. TX4B235 was marked for subsequent observation and noted as having exceptional characteristics. Two-year and older trees of the variety were subsequently evaluated during the 2006 through 2011 fruit growing seasons in both California (Clovis) and Texas (College Station, Fairfield, and Terrell).

Asexual Reproduction of the Variety

TX4B235 ('Royal Zest One') was bud grafted onto virus-free Nemaguard (not patented, Brooks and Olmo, 1997) peach rootstock in June 2003 at the nursery site in Oakdale, Calif. The variety was subsequently planted at the experimental orchard in the central portion of the San Joaquin Valley, near Fowler, Fresno County, Calif. and in three sites in Texas (College Station, Fairfield, and Terrell). Fruit from the resulting propagation has been evaluated during the period from 2006 to 2011 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographs. The fruit, pits, flowers, and shoots depicted are from mature trees that are 5 years of age.

BOTANICAL DESCRIPTION OF THE VARIETY

Figure 1:
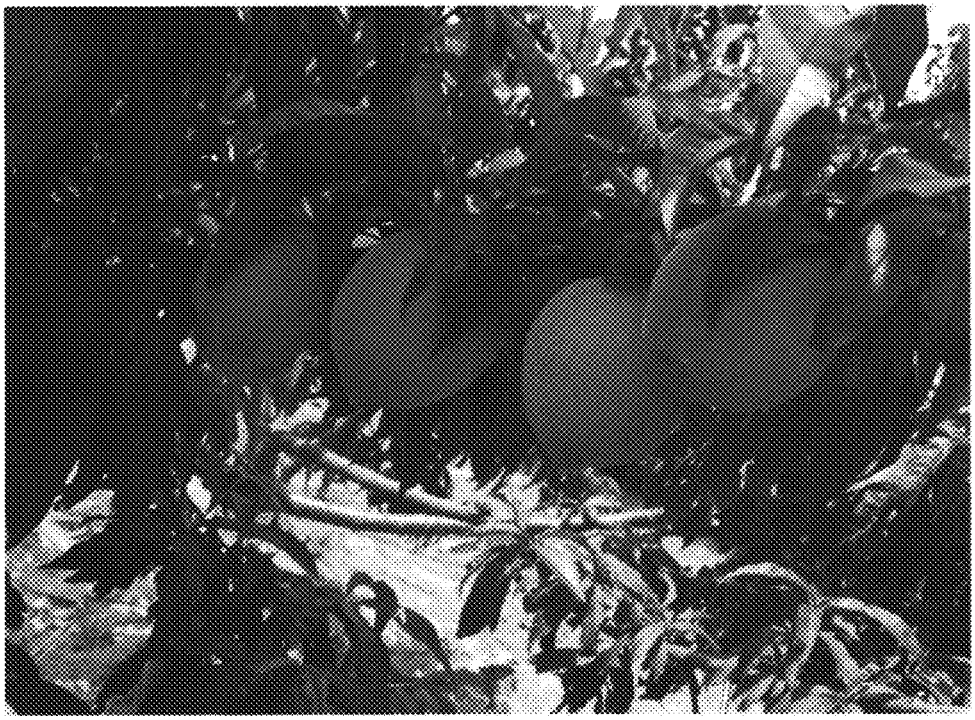
FIG. 1 A color photograph of a characteristic twig bearing typical leaves and several mature fruit showing their external coloration sufficiently matured for harvesting and shipment of 'Royal Zest One'. The shape of the fruit is slightly elongated because it was a low chill year.
Figure 2:
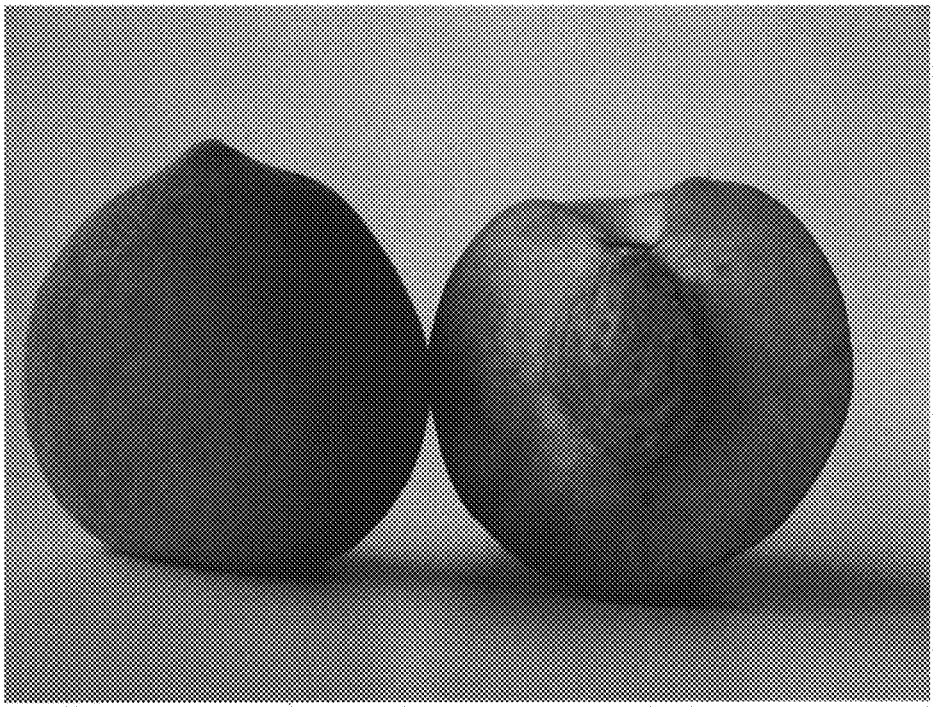
FIG. 2. Color picture showing the flesh and skin color and fruit shape of 'Royal Zest One' produced in the medium chill zone of Texas (Fairfield).
Figure 3:
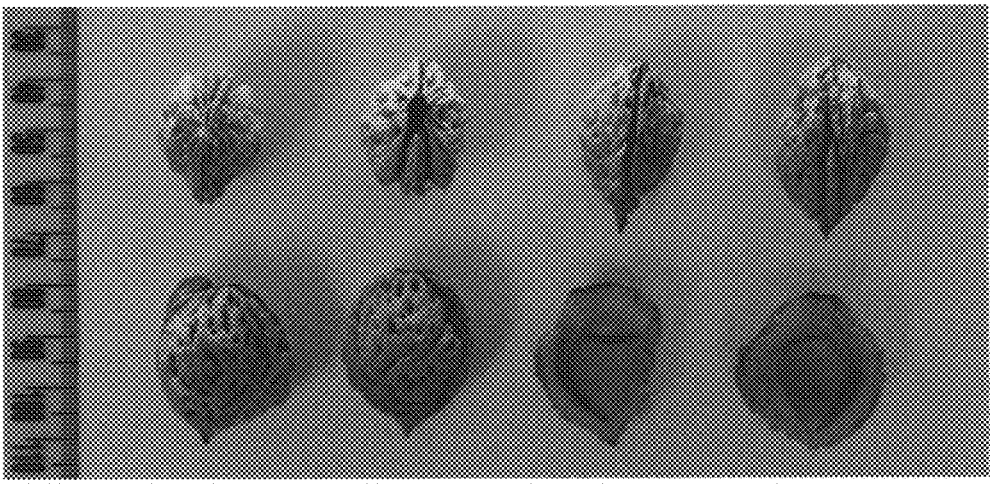
FIG. 3. Color photograph of the endocarp of 'Royal Zest One'. The ruler is demarcated in millimeters.
Figure 4:
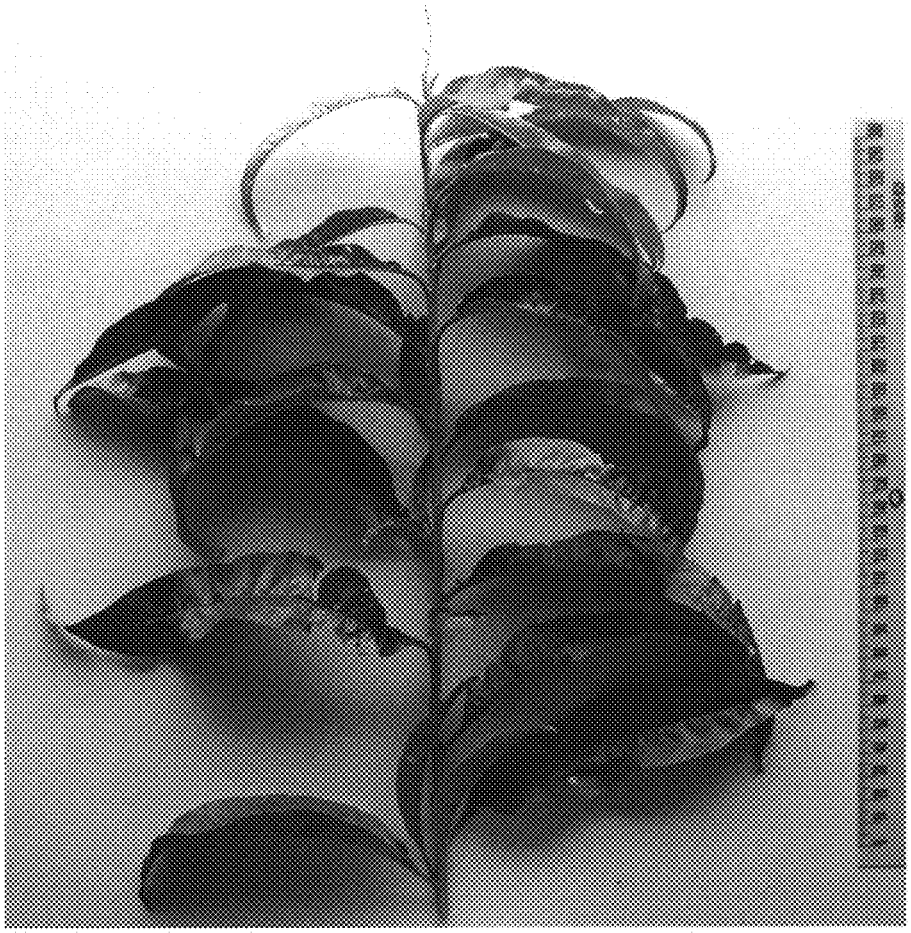
FIG. 4. A stem showing the leaves of the 'Royal Zest One' peach. The ruler is demarcated in millimeters.
Figure 5:
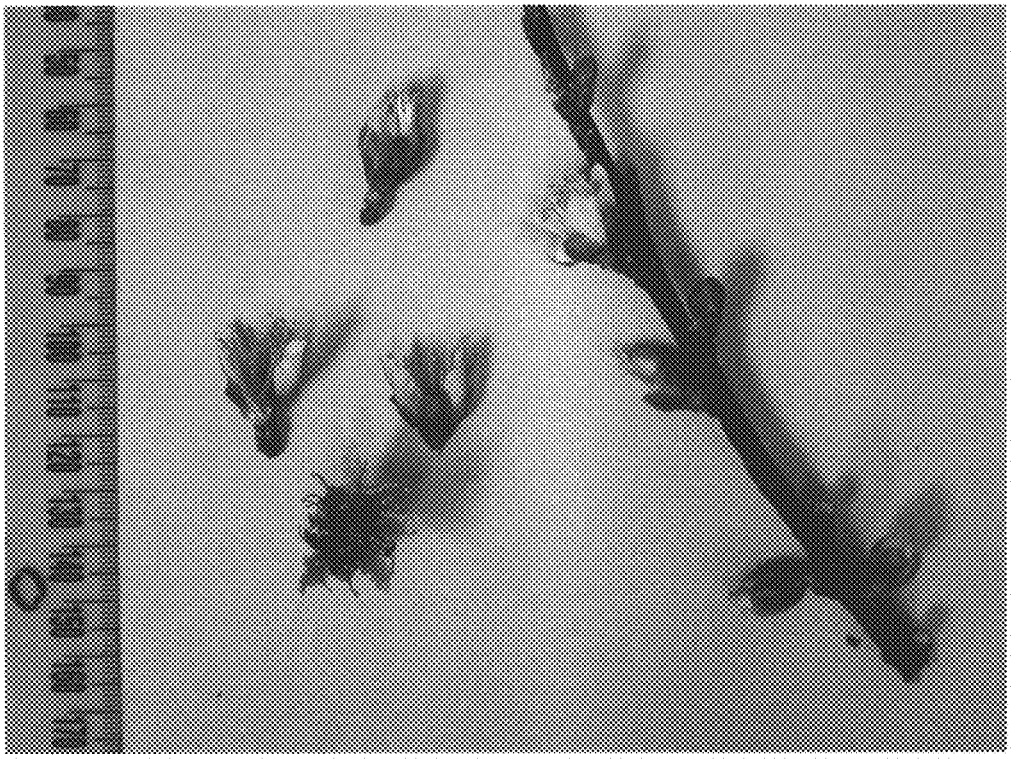
FIG. 5. The non-showy flowers of 'Royal Zest One'. The ruler is in millimeters.

Referring more specifically to the pomological details of this new and distinct variety of peach tree, the following has been observed under the ecological conditions prevailing at the experimental orchards in the medium chill zone of Texas (Fairfield and College Station, Tex.) on mature five-year old peach trees. All major color code designations are by reference to The R.H.S. Colour Chart (2001) and The R.H.S. Mini Colour Chart (2005) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the early season of maturity.

*Height*.—7 feet (2.13 m) on five-year old trees pruned to an open center training system.

*Width*.—7 feet (2.13 m) on five-year old trees pruned to an open center training system.

*Vigor*.—High.

*Density*.—Medium to high.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (Byrne and Bacon, 1991).

*Current season growth*.—The current season growth for the new variety was approximately 3.0 to 3.3 feet (0.91-1.12 m).

*Regularity of bearing*.—Regular, and considered hardy under typical conditions experienced in the medium chill zone of central Texas (College Station, Fairfield, Terrell, (USDA Hardiness zones 8a and 8b) and in central San Joaquin Valley in Calif. (USDA Hardiness zones 9b).

Trunk:

*Size*.—Approximately 3.3 inches (8.38 cm) in diameter and 11.0 inches (27.9 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, R.H.S. colors present are 197B-C of the Greyed-Green Group, 199C-D of the Grey-Brown Group, N200D of the Brown Group and 201D of the Grey Group.

Branches:

*Size*.—Considered medium for the variety.

*Thickness*.—Average (about 5.5 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 3 to 5 mm in width and were approximately 1-2 mm in height.

*Current season shoots*.—Surface texture — Substantially glabrous.

*Internode length*.—Approximately 1.5 to 4.0 cm as measured in the middle of a current season stem.

*Color of mature branches*.—The predominant R.H.S. colors are 166A and 176A-B of the Greyed-Orange Group and N200C-D of the Brown Group.

*Current season shoots*.—Color (R.H.S. colors) — Light green (139D and 142B of Green group and 144A, 144B and 144C of the Yellow Green Group) with some reddish-brown coloration appearing on exposed surface of the shoots (174C-D of the Grey Orange group). The color of new shoot tips is considered a bright and shiny green (mainly RHS Green Group 142B).

Leaves:

*Size*.—Considered average for the species. Leaf measurements have been taken from vigorous upright current season growth approximately at mid-shoot.

*Leaf length*.—Approximately 158 to 173 mm.

*Leaf width*.—Approximately 36 to 42 mm.

*Leaf thickness*.—Less than 1 mm.

*Leaf form*.—Lanceolate.

*Leaf tip form*.—Acuminate.

*Leaf upper surface color*.—Green, approximately 137A of the Green Group.

*Leaf lower surface color*.—Green, approximately 147B of the Yellow-Green Group.

*Leaf mid-vein color*.—Light green, approximately 145B of the Yellow-Green Group.

*Leaf margins*.—Form — Considered crenate/crenulate. Uniformity — Considered generally uniform.

*Leaf petioles*.—Size — Considered medium. Length — Approximately 8 to 13 mm. Thickness — Approximately 1 to 2 mm. Color — Pale green (145A of the Yellow-Green Group).

*Leaf glands*.—Size — Approximately 1 mm in height and 1 to 1.5 mm in width. Number — Generally 0-2 per leaf. Type — Reniform. Color — Brown (N199C of the Grey-Brown Group).

*Leaf stipules*.—Size — Medium for the species. Length — Approximately 10-15 mm. Form — Lanceolate.

*Color*.—Light green (RHS Yellow-Green 145B) with reddish brown tips (RHS Greyed-Orange Group 174C) when young. The stipules are deciduous.

*Ratio of wood (leaf) buds to flowering buds*.—1 to 2 flower buds per vegetative bud.

Flowers:

*Floral buds*.—General — The floral buds are considered to be of average size, conic form, and slightly appressed relative to the bearing shoot. Color — The bud scales are light gray-brown, (approximately RHS Greyed Green Group 195A and 197A and Grey Brown Group N199B). The buds are considered hardy under typical conditions found in the medium chill zone of Texas and the central San Joaquin Valley, Calif. climatic conditions. Length — Approximately 5 to 7 mm. Blooming Type — Considered medium early in relation to other peach cultivars commonly growing in the medium chill zone of Texas. Date of full bloom was between February 26th and March 10th during the period between 2006 and 2011. Mean bloom date was March 4th which is about 7 days before 'June Gold' is in full bloom. Flower Type — Non-showy. Flower Size — Flower diameter at full bloom is approximately 17 to 19 mm. Bloom Quantity — Considered abundant. Flower Bud Frequency — Normally 1 to 2 per node.

*Petal size*.—General — Considered small for the species. Width — Approximately 5 to 9 mm. Length — Approximately 14-15.5 mm. Petal Form — Broadly ovate. Petal Count — Nearly always 5. Petal Color — Medium pink when young (Red-Purple Group 62A-D), becoming darker with age.

*Petal claw*.—Form — The claw is considered present and has a small size when compared to other varieties. Length — Approximately 0.5 to 1 mm. Width — Approximately 0.5 to 1 mm. Petal Margins — Generally considered variable, from nearly smooth to slightly undulate. Petal Apex — Generally — The petal apices appear slightly rounded.

*Flower pedicel*.—Length — Considered long, and having an average length of approximately 4 to 4.5 mm. Thickness — Considered average, less than 1 mm. Color — A light green (Yellow-Green Group 144C-D).

*Floral nectaries*.—Color — Bright orange to orange-gold (Yellow-Orange Group 23A-B, 24A and N25A-C).

*Hypanthium*.—Surface Texture — Generally glabrous. Color — A purplish red (approximately Red-Purple Group 59A-C and 60A).

*Sepals*.—Surface Texture — The surface has a short, fine, wooly and a gray-colored texture. Size — Average and ovate in form. Color — A dull red (approximately Red-Purple Group 59A-C).

*Anthers*.—General — Average in size for the species. Color — Young anthers are yellow (approximately Yellow Group 10B-C and 11C-D) with red on edge (approximately Orange-Red Group 31A-C). Pollen Production — Pollen is abundant, and is a yellow color. Tree is self-fertile.

*Filaments*.—Size — Variable in length, approximately 15 to 17 mm, with the filaments slightly longer than the pistil. Color — White (approximately White Group N999D, R.H.S. Mini Colour Chart, 2005) and darkening to purplish-red with advanced maturity (approximately Red-Purple Group 70A-C).

*Pistil*.—General — Average in size, but slightly shorter, relative to the general anther height, overall. Length — Approximately 14 to 17 mm (including the ovary). Color — Considered white with light green when young (approximately White Group 155A-D, Green-White Group 157A-D and Greyed-Yellow Group 160A-C), and becoming darker with advancing senescence (approximately Red-Purple Group 65 A-D). Surface Texture — The variety has a long, silver white pubescent pistil and pubescent ovary (approximately White Group 155A-D).

Fruit:

*Maturity when described*.—The present variety of fruit is described, as it would be found in its firm ripe condition at full commercial maturity. Under the ecological conditions prevailing in the medium chill zone of Texas 'Royal Zest One' ripens in mid to late May, a few days before 'Regal' and about 2 weeks before 'June Gold'.

*Size*.—General — Medium large to large for the season and considered uniform.

*Average cheek diameter*.—Approximately 57 to 61 mm.

*Average suture diameter*.—Approximately 55 to 58 mm.

*Average axial diameter*.—Approximately 55 to 60 mm.

*Fruit form*.—Generally quite ovate in its lateral aspect. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Color — The suture normally is the same color as the underlying blush (Orange-Red Group N34A and Greyed-Orange Group 173A). Ventral Surface — Form — Considered uniform.

*Stem cavity*.—Size — Considered medium for the species. Width — Approximately 9 to 12 mm. Length — Approximately 13 to 25 mm. Depth — Approximately 6 to 7 mm. Fruit Base — Generally considered round and uniform. Fruit Apex — Generally considered flat and round.

*Fruit stem*.—Generally — Considered medium in length, approximately 8 to 9 mm. Thickness — Approximately 3 to 4 mm. Color — Generally a pale yellow-green (Yellow-Green Group 144A-B).

*Fruit skin*.—Generally considered medium or average in thickness. Surface Texture — The variety has very light, short pubescence. Skin Acidity — Considered neutral. Tenacious to Flesh — Yes at commercial maturity. Tendency to Crack — Not observed. Skin Color — Generally — Variable, with approximately 40-80% of the fruit surface covered with an attractive orange red blush. Down — Light and short. Blush Color — The blush color is generally more prevailing apically. This red blush ranges from an orange red (Orange Red 34A-D and Greyed-Red Group 178A-D) with many degrees of shading and blending occurring between these colorations. Skin Ground Color — The skin ground is a soft yellow color (approximately Yellow-Orange Group 18A-B). Flesh Color — Generally considered variable from yellow near the stone (Yellow Group 8A-D) with flecks of red appearing near the outer edge (Orange-Red Group N34A and Greyed-Red Group 179A). Flesh Fibers — Present, numerous and lightly colored. These fibers are present throughout the flesh. Stone Cavity Color — Generally considered variable from a medium yellow to light yellow color (Yellow Group 8A-D). Flesh Texture — Generally, the flesh is considered firm and fine at commercial maturity. Ripening — Generally the fruit of the present variety ripens evenly. Flavor — Considered sweet and with a slightly acidic flavor. Aroma — Pleasant and reasonably abundant. Eating — Generally considered very good, particularly for an early ripening variety.

Stone:

*Attachment*.—Clingstone at commercial maturity.

*Stone size*.—Generally considered medium-large relative to the ratio of stone to fruit size. Length — Approximately 31 to 35 mm. Width — Approximately 26 to 27 mm. Thickness — Approximately 18 to 19 mm. Fibers — Generally numerous fibers are attached along the entire surface of the stone. Stone Form — Generally the stone is considered oblate. Stone Base Angle — The stone is considered wide. Apex Shape — The stone apex is medium. Stone Shape — Considered variable, from ovid to elongated.

*Stone surface*.—Surface Texture — Minor surface markings are honeycombed with numerous single pits, chains of pits and pit grooves. Ventral Edge — Considered medium in size. Dorsal Edge — Shape — Grooved and having moderately rough edges. Stone Color — The color of the dry stone is light brown (161D of the Greyed-Yellow Group and 164D and 165D of the Greyed-Orange Group). The color of the inside surface of the endocarp is primarily 159A of the Orange-White Group and 164D and 165D of the Greyed-Orange Group. Tendency to Split — Splitting is relatively uncommon. Kernel — the kernel fills the endocarp at harvest. When dried the shriveled kernels measure approximately 1-2 mm in thickness, 7-9 mm in width, and 12-15 mm in length. The colors of the shriveled kernels are primarily Greyed-Orange Group 165B-C. Use — The subject variety, 'Royal Zest One', is considered to be a peach tree of early-season maturity, which produces fruit which are firm, attractively colored, and which are useful for the regional fresh fruit market. Keeping Quality — Good. Resistance to Insects and Disease — No observations were made on susceptibility or resistance to any disease or insect. Shipping Quality — Average. Although the new variety of peach tree possesses the described characteristics when grown under the ecological conditions prevailing near Fairfield, Freestone county, Tex. it will be understood that variations of the usual magnitude and characteristics incident to the changes in growing conditions, fertilization, pruning, and pest control are to be expected.

References

Andrews, C. P., W. B. Sherman, and P. M. Lyrene, 1979. 'Flordaking' peach. HortScience 14:81-82.

Anon. 2001. R.H.S. Colour chart. The Royal Hort. Soc., London.

Anon. 2005. R.H.S. Mini Colour chart. The Royal Hort. Soc., London.

Brooks, R. M. 1958. Double Delight, Earligold, and June Gold peaches. Fruit Var. J. 3:22 (U.S. Plant Pat. No. 1,884).

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Zaiger, C. F., G. N. Zaiger, L. M. Gardner and G. Grant. 1988. Peach tree "Amparo". U.S. Plant Pat. No. 6,472. Dec. 20, 1088.

Zaiger, C. F., G. N. Zaiger, L. M. Gardner, and G. G. Zaiger. 1990. Peach tree 'Rich Lady'. U.S. Plant Pat. No. 7,290. Aug. 7, 1990.

We claim:

1. A new and distinct *Prunus persica* tree, substantially as illustrated and described herein.

* * * * *